United States Patent [19]

Dubner

[11] Patent Number: 5,276,235
[45] Date of Patent: * Jan. 4, 1994

[54] RESIDUAL STREAM UPGRADING IN A PROPYLENE OXIDE-STYRENE MONOMER PROCESS

[75] Inventor: Walter S. Dubner, Wilmington, Del.

[73] Assignee: ARCO Chemical Technology, L.P., Wilmington, Del.

[*] Notice: The portion of the term of this patent subsequent to May 11, 2010 has been disclaimed.

[21] Appl. No.: 19,944

[22] Filed: Feb. 19, 1993

[51] Int. Cl.⁵ .............................................. C07C 1/20
[52] U.S. Cl. ............................ 585/469; 585/435; 585/437; 585/805; 585/905; 549/523; 549/525; 549/529
[58] Field of Search ............... 585/435, 437, 469, 805, 585/807, 833, 905; 549/523, 524, 529, 572, 573

[56] References Cited

U.S. PATENT DOCUMENTS

| | | | |
|---|---|---|---|
| 3,351,635 | 11/1967 | Kollar | 260/348.5 |
| 3,439,001 | 4/1969 | Pell et al. | 260/348.5 |
| 3,819,663 | 6/1974 | Levine et al. | 549/529 |
| 4,066,706 | 1/1978 | Schmidt | 260/610 |
| 4,093,636 | 6/1978 | Bost et al. | 549/529 |
| 4,262,143 | 4/1981 | Becker | 568/574 |
| 4,375,570 | 3/1983 | Yudovich | 585/476 |
| 5,210,354 | 5/1993 | Dubner et al. | 585/469 |

Primary Examiner—Helen M. S. Sneed
Assistant Examiner—P. Achutamurthy
Attorney, Agent, or Firm—William C. Long

[57] ABSTRACT

In the co-production of propylene oxide and styrene monomer, there is produced a sodium-containing heavy residue stream previously suitable only as a low grade fuel. In accordance with the invention, the heavy residue stream is contacted with acid having a molar concentration with respect to water above that which corresponds to the product salt solubility limit, and the resulting mixture is phase separated into an aqueous sodium salt-containing slurry phase and an organic phase reduced in sodium.

3 Claims, 1 Drawing Sheet

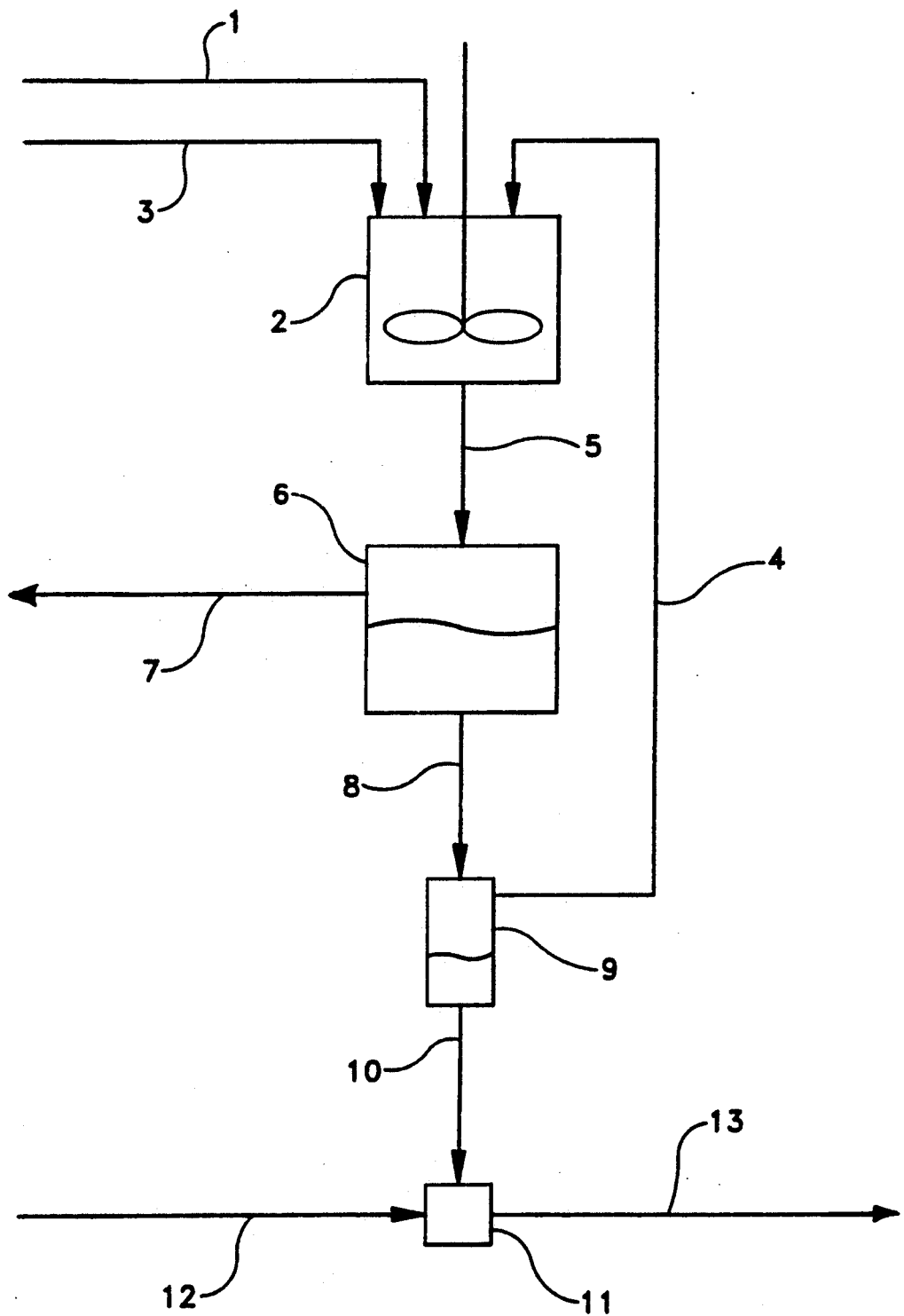

RESIDUAL STREAM UPGRADING IN A PROPYLENE OXIDE-STYRENE MONOMER PROCESS

BACKGROUND OF THE INVENTION

Related Application

Co-pending application Ser. No. 07/880,836 filed May 8, 1992 now U.S. Pat. No. 5,210,354 relates to an improved recovery of 1-phenyl ethanol and styrene from heavy residual process streams from the propylene oxide and styrene monomer process. The process of said copending application Ser. No. 07/880,836 involves acid treatment and cracking of the heavy residual process stream.

The present invention relates to improvements in the acid treatment step such as is employed in said co-pending application.

Field of the Invention

The present invention relates to the improved acid treatment of heavy residual process streams from the co-production of propylene oxide and styrene monomer and especially to a process wherein the sodium salts resulting from the acid treatment are separated as an aqueous slurry from the treated organic stream.

Description of the Prior Art

An extremely successful process for the co-production of propylene oxide and styrene monomer involves the molecular oxygen oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to styrene monomer. The basic patent describing this process is U.S. Pat. 3,351.635.

In practice of the process, various distillation steps are employed in order to separate unreacted reagents as well as various product streams, and generally one or more caustic treatment steps are employed in order to reduce the acidic characteristics of various streams.

In commercial practice of the propylene oxide-styrene monomer process there is formed a heavy residue stream containing, as a result of one or more caustic treatments, relatively high levels of sodium compounds. Heretofore, such heavy residue has comprised a low value product stream suitable only for use as a low grade fuel.

In accordance with the invention described in co-pending application Ser. No. 07/880,836, the disclosure of which is incorporated herein by reference, a process is provided whereby the low value product stream is upgraded and valuable products are recovered therefrom. The said process involves treating the low value stream with aqueous acid and phase separating the resulting mixture into an aqueous phase containing most of the sodium previously associated with the low value stream and an organic stream phase having reduced sodium content. The resulting organic stream phase can be directly cracked at elevated temperature with the formation of 1-phenyl ethanol and styrene or the organic stream phase can be passed to a wiped film evaporator where a volatile stream is separated and cracked to form 1-phenyl ethanol and styrene, the heavy stream from the evaporator comprising a useful fuel.

BRIEF DESCRIPTION OF THE INVENTION

In accordance with the present invention, there is provided a further improvement in the above-described process. Specifically, it has been found that substantial improvements in the amount of water employed and in a reduced organic contamination of aqueous streams is achieved where the acid employed in treatment of the sodium-containing organic residue stream is used in a molar concentration which corresponds to a product salt concentration which is above the salt solubility limit in the aqueous treating stream. By virtue of operation in this fashion, product solid is formed in the mixed system and settles to form a slurry in the aqueous treating stream. High density differences between the aqueous and organic phases are achieved thus facilitating separation of the phases. Product salts in crystalline form substantially free of contaminating organic are readily recovered, and the recovered material can be treated in conventional waste treatment processes.

DESCRIPTION OF THE DRAWING

The attached drawing illustrates in schematic form a practice of the invention.

DETAILED DESCRIPTION

The overall process to which the invention is applied is described in co-pending application Ser. No. 880,836. As described therein, in a first reaction step, ethyl benzene is reacted with molecular oxygen at elevated temperature in accordance with known techniques to form ethyl benzene hydroperoxide. U.S. Pat. 4,066,706 provides a comprehensive description of this reaction.

Suitably, a small amount of alkali is incorporated in the oxidation mixture as provided in U.S. Pat. 4,262,143 in order to improve oxidation rate and selectivity. Ethyl benzene hydroperoxide is reacted with propylene to form propylene oxide and 1-phenyl ethanol. U.S. Pat. 3,351,635 describes suitable conditions and catalysts for this reaction.

The epoxidation reaction mixture is generally caustic washed and subjected to a series of distillations in order to separate materials contained therein. Generally, the reaction mixture is first distilled to separate unreacted propylene overhead from heavier components. The separated propylene is conveniently recycled to the epoxidation step.

The heavier components are then further distilled after caustic wash in a series of distillations to separate unreacted ethyl benzene which can be recycled, preferably after a caustic wash as described in U.S. Pat 3,439,001, product propylene oxide, and product 1-phenyl ethanol leaving a heavy organic sodium-containing low value product stream.

The 1-phenyl ethanol stream is dehydrated to product styrene monomer in accordance with known procedures such as described in U.S. Patent 3,351,635.

In accordance with the process of Ser. No. 07/880,836, the sodium-containing low value organic product stream is treated in order to upgrade the stream and to recover valuable products therefrom.

In one embodiment, the low value product stream is thoroughly admixed with aqueous acid, preferably sulfuric acid, at relatively mild conditions, e.g. 20–100° C., preferably 40°–90° C. The resulting mixture is separated into immiscible phases, specifically an aqueous sodium-containing phase and an organic phase having reduced sodium content.

The organic phase has added thereto a compatible acid catalyst such as p-toluene sulfonic acid and the resulting mixture is cracked at elevated temperature to form 1-phenyl ethanol and styrene monomer which products can be separated by distillation from remaining heavy materials. Conditions for the cracking include temperatures of 70° C. to 300° C., preferably 120° C. to 220° C. and pressures below atmospheric, e.g. 100—400 m.m.Hg. which are appropriate for vaporization of light materials.

Product 1-phenyl ethanol and styrene monomer from the cracking represent increased yields of desired products of the overall process. Also, the heavy materials from the cracking are useful as fuel.

In another, more preferred practice, the organic phase from the acid treatment is subjected to a wiped film evaporation in order to separate up to about 40% by weight of the stream as volatile overhead fraction. This overhead fraction can be passed directly to the 1-phenyl ethanol dehydration step employed in commercial propylene oxide/styrene monomer processes wherein components of the volatile overhead are converted to styrene monomer at the conditions conventionally employed for the 1-phenyl ethanol dehydration.

The heavy bottoms from the wiped film evaporation is, itself, useful as an upgraded fuel by virtue of the low sodium content thereof.

The acid employed in the heavy organic treatment is preferably sulfuric acid. Other less preferred acids are phosphoric acid, oxalic acid and the like.

The acid is used in at least an amount sufficient to react with all of the sodium in the heavy organic stream. In the case of sulfuric acid, sufficient acid is used to form sodium sulfate, i.e. 0.5 mol of sulfuric acid per mol of contained sodium, and preferably at least 1 mol sulfuric acid per mol of sodium are employed sufficient to form sodium bisulfate. Where other acids are used, equivalent amounts are employed.

In accordance with the present invention, a critical feature lies in the provision that the acid employed to react with the sodium-containing heavy organic stream is employed in a molar concentration which corresponds to product sodium salt concentrations above the salt solubility limit in the aqueous phase resulting from the treatment. In this way, the salt products of the reactive treatment are formed as a slurry in the mixed phase which in turn results in a maximized density difference between the phases, a greater ease of separation, and a reduced organic contamination of the slurry components.

The invention can be described with reference to accompanying FIG. 1 which is a schematic representation of a practice of the process.

The heavy sodium-containing residual organic stream passes via line 1 to mixing zone 2 wherein it is admixed with acid such as sulfuric acid introduced via line 3. Optionally, there is provided a recycle aqueous stream introduced via line 4.

Some water may be contained with the acid which is introduced via line 3, but it is essential to successful practice of the invention that the molar concentration of acid introduced via line 3 must correspond to the product salt concentrations above the salt solubility limit. In other words, any water introduced with the acid via line 3 must be insufficient to completely solubilize formed sodium salts.

The acid introduced via line 3 can be 100% acid by weight; however, generally commercially available acid of 93—96% by weight concentration are preferred by reason of cost; aqueous acid comprised of at least 25 wt. % acid can be used.

Aqueous recycle stream which may be introduced into mixing zone 2 via line 4 is essentially an aqueous saturated salt solution.

The streams are thoroughly mixed in zone 2 and the admixture passes via line 5 to decantation zone 6. Sodium salts which are formed in zone 2 by the reaction of acid and the sodium components of the heavy organic residue stream are deposited as insoluble crystals in the lower aqueous phase. The upper organic phase, substantially purified with respect to sodium, is decanted and removed from zone 6 via line 7. An aqueous phase comprising an aqueous slurry of sodium salts is removed via line 8.

By virtue of the high density difference between the organic phase and the aqueous slurry phase, a very good separation of these phases is achieved in decantation zone 6.

The aqueous slurry passes via line 8 to separation zone 9 wherein crystal solids are separated from the aqueous liquid by conventional means. The aqueous may be passed via line 4 to mixing zone 2 as described above.

The salt crystals pass via line 10 to mixing zone 11 wherein the said concentration can be adjusted by the introduction of water via line 12 and the resulting salt solution passes via line 13 to conventional processing. A feature of the invention is that the organic content of the salt solution is sufficiently reduced that the solution can be bio-treated in conventional fashion without further pretreatment. Optionally, the crystals can be recovered as such without water dilution.

EXAMPLE

The following example, which is described with reference to the accompanying drawing, illustrates the invention.

A heavy organic residue stream from the propylene oxide styrene monomer technology is produced as described in co-pending application Ser. No. 07/880,836. The bottoms stream is primarily comprised of oxygenated aryl compounds with molecular weights greater than 225 g/mol. and contains about 0.7 wt. % sodium. The heavy stream passes via line 1 to mixing zone 2 at the rate of 7,000 lbs./hr. Also introduced into zone 2 via line 3 is sulfuric acid in the form of a 96 wt. % aqueous sulfuric acid stream which is introduced at the rate of 220 lbs./hr. A recycle aqueous stream saturated in sodium bisulfate is introduced into zone 2 by means of line 4 at the rate of 600 lbs./hr. This flow rate may be adjusted to change the organic/aqueous phase ratio and other physical characteristics of the admixture.

From mixing zone 2 the admixture passes via line 5 to separation zone 6 wherein the various layers are separated by decantation. The upgraded organic stream of about 6950 lbs./hr. passes from zone 6 via line 7 and represents a substantially upgraded heavy residue stream containing 40 ppm sodium. This stream is well suited for treatment to recover 1-phenyl ethanol and styrene values as described in said co-pending application.

The aqueous phase from zone 6 comprises a slurry of crystals which are mainly sodium bisulfate in an aqueous saturated solution of sodium bisulfate. The aqueous phase contains organic impurities expressed as carbon content of about 1.2–1.5 wt. %. This phase is separated via line 8 and passes to separation zone 9 wherein the solid crystals in amount of about 255 lbs./hr. are separated from the supernatent aqueous liquid which can be recycled to zone 2 by means of line 4. The organic impurities content of the recovered crystals expressed as carbon content is reduced to about 0.2 wt. %. The crystals are separated from zone 9 via line 10 and pass to zone 11 herein the crystals can be redissolved in water which is introduced via line 12 at the rate of 750 lbs./hr. The sodium bisulfate aqueous solution is removed from zone 11 by means of line 13, and this stream can be directly treated in accordance with known biotechnical procedures for the ultimate waste disposal. Optionally, the sodium bisulfate crystals can be recovered as such.

What is claimed:

1. In a process for the coproduction of propylene oxide and styrene monomer wherein ethylbenzene is oxidized to ethylbenzene hydroperoxide, said hydroperoxide is reacted with propylene to form propylene oxide and 1-phenyl ethanol, unreacted propylene, propylene oxide and 1-phenyl ethanol are separately recovered by distillation leaving a heavy residue containing sodium which is present as a result of caustic treatment of one or more of the process streams and oxygen-containing organic materials formed in the process, and the 1-phenyl ethanol is dehydrated to styrene monomer, the improvement which comprises admixing the said heavy residue with acid, the molar concentration of which corresponds to a molar product sodium salt concentration above the solubility limit, and phase separating the resulting admixture into an aqueous sodium salt-containing slurry phase and an organic phase having a reduced sodium content.

2. The process of claim 1 wherein the said acid is sulfuric acid.

3. The process of claim 1 wherein said acid is 93–100 wt. % sulfuric acid.

* * * * *